United States Patent [19]

Hubner et al.

[11] 4,053,624
[45] Oct. 11, 1977

[54] INDOLE-2-CARBALDEHYDE COMPOUNDS AND BLOOD SUGAR REDUCING COMPOSITIONS

[75] Inventors: Manfred Hubner, Ludwigshafen (Rhine); Ruth Heerdt, Mannheim-Feudenheim; Felix Schmidt, Mannheim-Seckenheim; Max Thiel, Mannheim, all of Germany

[73] Assignee: Boehringer Mannheim GmbH, Mannheim, Germany

[21] Appl. No.: 573,214

[22] Filed: Apr. 30, 1975

[30] Foreign Application Priority Data

May 31, 1974 Germany .............................. 2426439

[51] Int. Cl.$^2$ .................... A61K 31/40; C07D 209/12
[52] U.S. Cl. ........................... 424/274; 260/326.13 R; 260/326.16
[58] Field of Search .................... 260/326.16; 424/274

[56] References Cited
PUBLICATIONS

Dambal et al., "Chem. Abstracts", vol. 62, p. 16,177e (1965).

Hirata et al., "Tetrahedron Letters", vol. 1969 (1), pp. 19-20 (1969).
Bhat et al., "J. Indian Chem. Soc.", vol. 51(3), pp. 427-429 (Mar. 1974).

*Primary Examiner*—Dolph H. Torrence
*Attorney, Agent, or Firm*—Burgess, Dinklage & Sprung

[57] ABSTRACT

New indole-2-carbaldehyde compounds of the formula

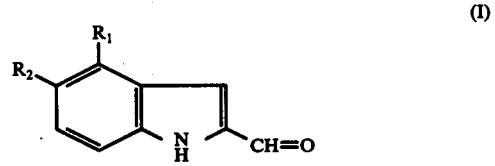

(I)

wherein
$R_1$ is lower alkyl
$R_2$ is hydrogen, halogen, or lower alkyl or alkoxy, with the proviso that when $R_2$ is halogen or ethyl, $R_1$ can also be hydrogen and the physiologically compatible derivatives thereof, are outstandingly effective in lowering excessive blood sugar in mammals.

15 Claims, No Drawings

INDOLE-2-CARBALDEHYDE COMPOUNDS AND BLOOD SUGAR REDUCING COMPOSITIONS

The present invention relates to new blood sugar lowering indole-2-carbaldehyde compounds and to therapeutic compositions and uses thereof.

Various substituted indole-2-carbaldehydes are described in the literature, but no blood sugar lowering effect has previously been ascribed to such compounds. (See, e.g., Chem. Abstracts, 75, 5620k; 70, 77690c; and 62, 16177e).

We have now found that a group of previously unknown indole-2-carbaldehydes substituted in the 4- and/or 5-position surprisingly show a blood sugar lowering effect.

The invention thus provides novel indole-2-carbaldehyde compounds of the formula:

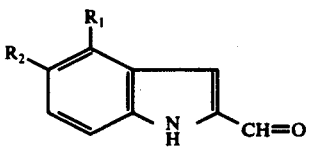

(I)

wherein
$R_1$ is lower alkyl
$R_2$ is hydrogen, halogen, or lower alkyl or alkoxy,
with the proviso that when $R_2$ is halogen or ethyl, $R_1$ can also be hydrogen
and the physiologically compatible derivatives thereof.

The invention further provides pharmaceutical prepartions containing such compounds and methods for reducing blood sugar utilizing them.

The lower alkyl or alkoxy radicals within the scope of the present invention encompass radicals containing up to 5 and preferably up to 2 carbon atoms. Halogen is to be understood to mean fluorine, chlorine and bromine, chlorine and bromine being preferred.

The new compounds according to the present invention can be prepared by known processes but preferably either by a. treating with suitable reducing agents an indole derivative of the general formula:

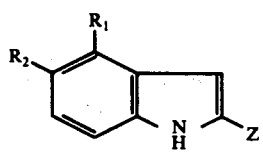

(II)

wherein
$R_1$ and $R_2$ have the same meanings as above, and
Z is a carboxyl group or their reactive derivatives;
or
b. treating an indole derivative of the general formula:

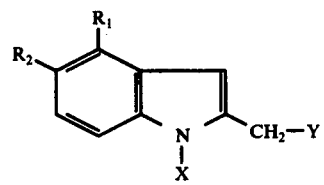

(III)

wherein
$R_1$ and $R_2$ have the same meaning as above, and
X is a hydrogen atom or a protective group,
Y is a hydrogen atom or a hydroxyl group,
with a suitable oxidation agent, whereafter, if necessary, the protective group X is split off and the aldehyde, if desired, is converted into a physiologically harmless derivative.

As physiologically harmless aldehyde derivatives of general formula I there can preferably be used acetals.

By reactive derivatives of carboxyl group Z there are meant the lower alkyl esters, mixed anhydrides, N-disubstituted amides, acid halogenides or the nitrile.

The protective group X can be, for example, an acyl radical which can be split off hydrolytically in known manner.

The starting materials of formula II can be obtained in known manner, preferably according to the so-called Reissert synthesis or the Fischer synthesis, whereby the initially formed carboxylic acids or esters are possibly converted in known manner into acid chlorides, anhydrides, amides or nitriles.

As reducing agent, there are used, for example, complex metal hydrides, whereby, according to the starting material used, there must be chosen between lithium or sodium aluminum hydride or their (gentler acting) di- or tri-alkoxy derivatives. Also boranes such as thexyl-borane (1,1,2-trimethylpropyl-borane) can be used, also catalytically active hydrogen in the known Rosenmund-reaction of the acid chlorides; preferably, one uses hydrazine which is first installed into the molecule in the form of a carboxylic acid hydrazide, whose tosyl derivative yields the desired aldehyde during heating with bases by nitrogen formation (reaction according to McFadyen-Stevens).

The starting materials of formula III can be obtained by means of the many processes developed for the synthesis of indole derivatives, the methods of Fischer, Madelung and Bischler being especially suitable.

As oxidation agents, there can be used, for example, sodium permanganate, manganese dioxide or chromium trioxide (especially as pyridine complex), but also other metallic or non-metallic compounds of higher oxidation stages.

The following examples are given for the purpose of illustrating the present invention:

EXAMPLE 1 — Preparation of 4-methylindole-2-carbaldehyde 25 g 4-methylindole-2-carboxylic acid ethyl ester (C.A. 52, 6314(a)) and 50 ml hydrazine hydrate were heated for six hours while stirring and under reflux at 120° C bath temperature. After cooling, the crystallized 4-methylindole-2-carboxylic acid hydrazide was filtered off with suction and washed thoroughly with ethanol.

Yield 23.0 g (= 98.5% of theory); melting point 269°–273° C.

23.0 g 4-methylindole-2-carboxylic acid hydrazide were added in small portions, while stirring and during ice cooling, to the solution of 23.0 g p-toluene sulfochloride in 300 ml pyridine. Then it was stirred for another hour in the ice bath and for another hour at room temperature, poured onto a mixture of 350 ml concentrated hydrochloric acid and ice, the precipitated 4-methylindole-2-carboxylic acid-(N'-tosyl-hydrazide) filtered off with suction and thoroughly washed with well diluted hydrochloric acid, then with water.

Yield: 38.3 g(= 92% theory); (melting point) 242°-245° C (decomposition).

38.0 g 4-methylindole-2-carboxylic acid-(N'-tosyl hydrazide) were added to the suspension preheated to 160° C of 38 g anhydrous soda in 380 ml ethylene glycol. The reaction took place with vigorous foaming. As soon as this stopped, the mixture was poured onto ice, the substance filtered off with suction, dissolved in toluene, the solution dried, carbonized and substantially concentrated. The 4-methylindole-2-carbaldehyde (crude yield about 43% of theory) was recrystallized twice from toluene.

Yield: 4.2 g (= 23.8% of theory); melting point 147°-149° C.

EXAMPLE 2 — Preparation of
5-methoxy-4-methylindole-2-carbaldehyde

VARIANT I

To a solution of 10 g 5-methoxy-4-methyl-2-hydroxymethyl-indole in 600 ml absolute methylene chloride there were added 25 g manganese dioxide (precipitated, active, to the synthesis, "Merck") and stirred for 10 hours at room temperature. Subsequently and after an additional 10 hours one added each time 5 g manganese dioxide. After a total of 30 hours one filtered off with suction and reduced the solution to dryness. The crude gross yield was 8.8 g (= 89% of theory), melting point 185°-187° C. In order to remove a brown impurity, one chromatographed over a short column with silicic gel 60 (Merck), as elution agent there was used heptane: methylethyl ketone = 4 : 1. After evaporation of the solvent one recrystallizes from toluene; the melting point then amounts to 187°-189° C.

VARIANT II

In a 500 ml three-necked flask with stirrer and a thermometer immersed in the fluid, one gradually adds 10 g chromium trioxide to 100 ml pyridine at 15°-20° C inside temperature then it is re-stirred for another hour. To this suspension of the yellow chromium trioxide-pyridine-complex one adds a solution of 8 g 5-methoxy-4-methyl-2-hydroxymethyl indole (melting point; 133°-135° C; from toluene) in 72 ml pyridine, stirs at room temperature for an additional two hours and let stand over night. Then one pours the solution onto the mixture of 200 ml concentrated hydrochloric acid and 500 g ice, filters the product precipitated thereby with suction, rewashes with water and recrystallizes (after drying) from toluene. The yield amounts to 3.7 g (= 47% of theory), the melting point is around 187°-189° C.

In analogous manner one obtains the following compounds a. from 4-methyl-2-hydroxymethyl-indole (melting point: 68°-70° C from tetrahydrofurane)
  4-methylindole-2-carbaldehyde
  m.p. 147°-149° C (from toluene)

b. from 5-ethyl-2-hydroxymethyl-indole (m.p.: 96°-98° C; from toluene)
  5-ethylindole-2-carbaldehyde
  m.p. 146°-148° C (from methanol/water)

c. from 4,5-dimethyl-2-hydroxymethyl-indole (m.p. 159° C; from ethyl acetate)
  4,5-dimethylindole-2-carbaldehyde
  m.p. 206°-207° C (from toluene)

d. from 5-chloro-4-methyl-2-hydroxymethyl-indole (m.p. 108° C; from toluene)
  5-chloro-4-methylindole-2-carbaldehyde
  m.p. 194°-196° C (from toluene)

e. from 5-ethoxy-4-methyl-2-hydroxymethyl-indole (m.p.: 152°-154° C; from toluene)
  5-ethoxy-4-methylindole-2-carbaldehyde
  m.p. 199°-201° C (from toluene)

f. from 5-bromo-2-hydroxymethyl-indole (m.p. 112°-116° C; from toluene)
  5-bromoindole-2-carbaldehyde
  m.p. 213°-215° C (from ethanol)

The 2-hydroxymethylindole derivatives used as starting compounds are produced from the corresponding indole-2-carboxylic acid esters by reduction with an excess of lithium aluminum hydride in absolute ether.

The blood sugar-lowering effectiveness of the indole-carboxylic acids according to the present invention was tested on rats and compared with 4-chloroindole-2-carbaldehyde, 5-methoxy-indole-2-carbaldehyde and 5-methylindole-2-carbaldehyde as conventional substances (Chem. Abstr. 75, 5620k; 70, 77690c; 62, 16177e).

The test compounds were administered as a solution in tylose to fasting male Spraque-Dawley rats with a body weight of 200–220 g. via a stomach tube. In the following Table 1, there is given the threshold dose which significantly lowers the blood sugar level for the test compounds of the invention as well as the known compounds identified above.

TABLE 1

| | Test Compound | Threshold Dosage |
|---|---|---|
| 1 | 4-Methylindole-2-carbaldehyde | 5 mg/kg |
| 2 | 5-Ethylindole-2-carbadehyde | 20 mg/kg |
| 3 | 5-Methoxy-4-methylindole-2-carbaldehyde | 10 mg/kg |
| 4 | 5-Ethoxy-4-methylindole-2-carbaldehyde | 30 mg/kg |
| 5 | 4-Chloroindole-2-carbaldehyde | >50 mg/kg |
| 6 | 5-Methoxyindole-2-carbaldehyde | >50 mg/kg |
| 7 | 5-Methylindole-2-carbaldehyde | 40 mg/kg |

As can be seen from the table the prior art compounds (to which no blood sugar depressing effectiveness had been ascribed in the prior art) are totally inactive or only very slightly active, relative to the very high activity of the compounds representative of the invention.

While the method of administering the active ingredients of the novel compositions of matter of the present invention is not limited to oral administration, a decided advantage of the present invention is that the active ingredients may be administered orally in any convenient manner. They may be taken orally for example, with an inert diluent or with an assimilable edible carrier, or they may be compressed into tablets, or enclosed in hard or soft gelatin capsules. Furthermore, the active ingredients may be administered either individually or as mixtures of a plurality of such active ingredients. The amount of a single dose or of a daily dose necessary to induce a particular level of hypoglycemia will vary with the size or weight of the warm-blooded animal to be treated.

Generally, it should be such as to give a proportionate dosage of from about 2.5 mg to about 25 mg per kg of body weight per day of, for example, 4-methylindole-2-carbaldehyde, a highly active compound, or other active ingredient or mixture thereof. In terms of total weight of active ingredient, the daily dosage for warm-blooded animals of, for example, 75 kilograms, would amount to from about 0.1 g to about 2.0 g. The dosage regimen may be adjusted to provide optimum therapeutic response; for example, several divided doses may be administered daily or the dose may be proportionately reduced or increased as the requirements of the therapeutic situation would indicate.

As blood lowering preparations according to the instant invention there can be used all known oral and parenteral application compositions such as tablets, capsules, dragees, syrups, solutions, suspensions, drops, suppositories or the like. For this purpose, the active material is mixed with solid or liquid absorbing substances (pharmaceutical diluent or carrier) and then brought into the desired form. Solid carrier materials include, for example, starch, lactose, mannitol, methyl cellulose, talc, highly dispersed silicic acid, high molecular weight fatty acids (for example stearic acid), gelatine, agar-agar, calcium phosphate, magnesium stearate, animal and vegetable fats and solid high molecular weight polymers (for example polyethylene glycols). Compositions suitable for oral administration can, if desired, contain flavoring and/or sweetening agents.

It will be understood that the specification and examples are illustrative but not limitative of the present invention and that other embodiments within the spirit and scope of the invention will suggest themselves to those skilled in the art.

What is claimed is:

1. Indole-2-carbaldehyde compound of the formula:

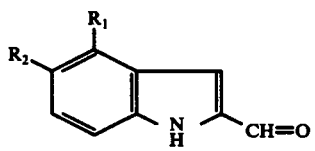

(I)

wherein
R₁ is lower alkyl of up to 5 carbon atoms and
R₂ is hydrogen, halogen or lower alkyl or alkoxy with the proviso that when R₂ is ethyl, R₁ may be hydrogen
and the physiologically compatible aldehyde derivatives thereof.

2. Indole-2-carbaldehyde compound as claimed in claim 1 wherein R₁ is alkyl of up to 5 carbon atoms.

3. Indole-2-carbaldehyde compound as claimed in claim 1 wherein R₂ is hydrogen.

4. Indole-2-carbaldehyde compound as claimed in claim 1 wherein R₂ is halogen selected from chlorine and bromine.

5. Indole-2-carbaldehyde compound as claimed in claim 1 wherein R₂ is alkyl of up to 5 carbon atoms.

6. Indole-2-carbaldehyde compound as claimed in claim 1 wherein R₂ is alkoxy of up to 5 carbon atoms.

7. Indole-2-carbaldehyde compound as claimed in claim 1 designated 4-methylindole-2-carbaldehyde.

8. Indole-2-carbaldehyde compound as claimed in claim 1 designated 5-methoxy-4-methylindole-2-carbaldehyde.

9. Indole-2-carbaldehyde compound as claimed in claim 1 designated 5-ethylindole-2-carbaldehyde.

10. Indole-2-carbaldehyde compound as claimed in claim 1 designated 5-ethoxy-4-methylindole-2-carbaldehyde.

11. Therapeutic composition for depressing blood sugar which comprises a pharmaceutically acceptable carrier and effective amounts of at least one indole-2-carbaldehyde compound as claimed in claim 1.

12. Method of depressing blood sugar in the subject which method comprises administering to such subject an effective amount of indole-2-carbaldehyde compound of the formula:

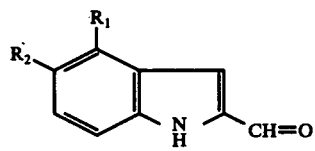

(I)

wherein
R₁ is lower alkyl or hydrogen and
R₂ is hydrogen, halogen or lower alkyl or alkoxy with the proviso that when R₂ is other than halogen or ethyl, R₁ is alkyl,
and the physiologically compatible aldehyde derivatives thereof.

13. Method as claimed in claim 12 wherein R₁ in the formula is lower alkyl.

14. Method as claimed in claim 12 wherein said compound is at least one selected from the group consisting of 4-methylindole-2-carbaldehyde, 5-methoxy-4-methylindole-2-carbaldehyde, 5-ethylindole-2-carbaldehyde and 5-ethoxy-4-methylindole-2-carbaldehyde.

15. Method as claimed in claim 12 wherein said compound is applied in an amount of from about 0.1 – 2.0 g per 75 kg of body weight of such subject.

* * * * *